United States Patent

Ninomiya et al.

[11] Patent Number: 6,080,896
[45] Date of Patent: Jun. 27, 2000

[54] PROCESS FOR PRODUCING POLYHYDRIC ALCOHOL

[75] Inventors: Teruyuki Ninomiya; Toshio Watanabe; Takaki Ikebe; Atsushi Iwamoto, all of Kurashiki, Japan

[73] Assignee: Mitsubishi Gas Chemical Company, Inc., Tokyo, Japan

[21] Appl. No.: 09/302,058

[22] Filed: Apr. 29, 1999

Related U.S. Application Data

[63] Continuation-in-part of application No. 09/118,419, Jul. 17, 1998.

[30] Foreign Application Priority Data

Aug. 7, 1997 [JP] Japan ..................................... 9-213480
Feb. 4, 1999 [JP] Japan ................................... 11-027425

[51] Int. Cl.⁷ ........................... C07C 29/38; C07C 31/22; C07C 47/21
[52] U.S. Cl. ............................................................. 568/853
[58] Field of Search ............................................. 568/853

[56] References Cited

U.S. PATENT DOCUMENTS 3,975,450  8/1976  Palmer et al. ........................ 260/635
4,514,578  4/1985  Immel et al. ............................ 568/853
5,608,121  3/1997  Ninomiya et al. ...................... 568/852

FOREIGN PATENT DOCUMENTS 0 708 073    4/1996  European Pat. Off. .
56-079632    6/1981  Japan .
63-139141    6/1988  Japan .

OTHER PUBLICATIONS

Terelak et al., Przem. Chem. (1994), 73(8), 296–7.
L. Cairate et al., "On the intermediates in the synthesis of trimethylolpropane", La Chemica E L'Industria, vol. 63, No. 11, pp. 723–725, Nov. 1981.

Primary Examiner—Laura L. Stockton
Attorney, Agent, or Firm—Frishauf, Holtz, Goodman, Langer & Chick, P.C.

[57] ABSTRACT

A process for producing a polyhydric alcohol with high selectivity by subjecting formaldehyde and a specific aliphatic aldehyde to an aldol condensation reaction in the presence of a base catalyst, and then subjecting the resultant reaction product to a crossed Cannizzaro reaction, while reacting a solution containing a 2-substituted-2-alkanal, formed as a byproduct during the aldol condensation reaction, with water or formaldehyde in the presence of the base catalyst, and thereafter reacting the resultant mixture with the aliphatic aldehyde.

13 Claims, No Drawings

PROCESS FOR PRODUCING POLYHYDRIC ALCOHOL

REFERENCE TO RELATED APPLICATION

This application is a continuation-in-part application of the application Ser. No. 09/118,419 filed Jul. 17, 1998.

BACKGROUND OF THE INVENTION

1. Field of the Invention

The present invention relates to a process for producing a polyhydric alcohol by reacting an aliphatic aldehyde with formaldehyde, which alcohol is useful as a raw material for polyester resins, alkyd resins, polyurethane resins, polycarbonate resins, plasticizers, surfactants, lubricating oils, basis for cosmetics, reactive monomers and the like.

2. Description of the Related Arts

There is described, as a process for producing a polyhydric alcohol, a two-stage reaction process in which an aliphatic aldehyde and formaldehyde are subjected to an aldol condensation reaction, and subsequently to a crossed Cannizzaro reaction each in the presence of a base catalyst, in Japanese Patent Application Laid-Open Nos. 139141/1988(Sho 63), 162538/1983(Sho 58), and U.S. Pat. No. 3,975,450, etc., said aliphatic aldehyde being represented by the following formula (I):

wherein R is a hydrogen atom or a straight-chain or branched aliphatic hydrocarbon group having 1 to 22 carbon atoms.

The above-mentioned two-stage reaction process is based on the premise that the objective polyhydric alcohol is produced in combination with a formic acid salt. Examples of the base catalyst to be used in said process include a hydroxide of any of alkali metals and alkaline earth meals, a carbonate of any of the above-mentioned metals, and alkylamines. The catalyst is exemplified by sodium hydroxide, potassium hydroxide, calcium hydroxide, sodium carbonate, potassium carbonate, calcium carbonate, and tertially amines such as trimethylamine, triethylamine, and tributylamine.

In general, a base catalyst comprising sodium hydroxide or calcium hydroxide is used in the process for producing a polyhydric alcohol by the reaction of an aliphatic aldehyde with formaldehyde. However, in order to obtain an objective polyhydric alcohol in high selectivity in the presence of the base catalyst comprising sodium hydroxide or calcium hydroxide, it is necessary to use formaldehyde in a large excess against the aliphatic aldehyde. In addition, in the case where such a large excess of formaldehyde is used, unless the reaction is carried out in a reaction system diluted with water, large amounts of byproducts are formed, thereby making it impossible to obtain the objective polyhydric alcohol in high selectivity.

There is also known a process for the production of a polyhydric alcohol by two-stage reaction process in which an aliphatic aldehyde and formaldehyde are subjected to an aldol condensation reaction, and subsequently to a crossed Cannizzaro reaction each in the presence of a carbonate catalyst. The process, however, leads to the by-production of about 10 mol % of 2-substituted-2-alkenal that is low in added values. Thus in order to suppress the by-production, it is also made necessary to use formaldehyde in a large excess against the aliphatic aldehyde.

The aforestated process that uses a large excess of formaldehyde involves the problem such that the production process is made intricate, since it is required to recover the used excess of formaldehyde from the viewpoints of economy and the influence of wastes and the like upon the environment.

In view of the above, a general object of the present invention is to provide a process for producing a polyhydric alcohol by subjecting an aliphatic aldehyde and formaldehyde to an aldol condensation reaction, and subsequently to a crossed Cannizzaro reaction, which process is characterized in that the objective polyhydric alcohol is produced in high selectivity using a slight excess of formaldehyde against the theoretical molar amount of the aliphatic aldehyde without dilution of the reactants with water.

SUMMARY OF THE INVENTION

Under such circumstances intensive research and investigation were made by the present inventors on the process for the production of a polyhydric alcohol involved with the above-mentioned subject. As a result, it has been found that the amount of aldehyde to be used can be decreased and an objective polyhydric alcohol can be obtained in high selectivity, by carrying out an aldol condensation reaction in the presence of a catalyst comprising a carbonate as a principal ingredient, and subsequently carrying out a crossed Cannizzaro reaction, while reacting 2-substituted-2-alkenal, which has been formed as a byproduct during the aldol condensation reaction, with water or formaldehyde in the presence of said base catalyst, and thereafter circulating the 2-substituted-2-alkenal to use it in the reaction, because said 2-substituted-2-alkenal is inferior in reactivity with said aliphatic aldehyde.

Specifically, the present invention relates to a process for producing a polyhydric alcohol which comprises subjecting formaldehyde and an aliphatic aldehyde represented by the general formula (I) to an aldol condensation reaction in the presence of a base catalyst comprising a carbonate as a principal ingredient, and subsequently subjecting the resultant reaction product to a crossed Cannizzaro reaction, while mixing a solution containing 2-substituted-2-alkanal-1 with formaldehyde in the presence of said catalyst, and thereafter reacting the resultant mixture with said aliphatic aldehyde being represented by the general formula (I), said 2-substituted-2-alkanal-1 being represented by the general formula (III) and being obtained by reacting 2-substituted-2-alkenal which has been formed as a byproduct during said aldol condensation reaction with water in the absence or the presence of said base catalyst or an acid catalyst, said 2-substituted-2-alkenal being represented by the general formula (II), wherein R is a hydrogen atom or a straight-chain or branched aliphatic hydrocarbon group having 1 to 22 carbon atoms.

And also, the present invention relates to a process for producing a polyhydric alcohol which comprises subjecting formaldehyde and an aliphatic aldehyde represented by the general formula (I) to an aldol condensation reaction in the presence of a base catalyst comprising a carbonate as a principal ingredient, and subsequently subjecting the resultant reaction product to a crossed Cannizzaro reaction, while mixing a solution containing a 2-substituted-2-alkanal-1 and a 2-substituted-2-alkanal-2 with formaldehyde in the presence of said catalyst, and thereafter reacting the resultant mixture with said aliphatic aldehyde being represented by the general formula (I), said 2-substituted-2-alkanal-1 being represented by the general formula (III) and said 2-substituted-2-alkanal-2 being represented by the general formula (IV), both of said 2-substituted-2-alkanal-1 and said 2-substituted-2-alkanal-2 being obtained by reacting 2-substituted-2-alkenal which has been formed as a byproduct during said aldol condensation reaction with aqueous solution of formaldehyde in the absence or the presence of a catalyst, said 2-substituted-2-alkenal being represented by the general formula (II), wherein R is a hydrogen atom or a straight-chain or branched aliphatic hydrocarbon group having 1 to 22 carbon atoms.

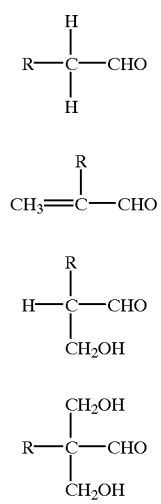

DESCRIPTION OF THE PREFERRED EMBODIMENTS

The reaction of an aliphatic aldehyde with formaldehyde for the purpose of producing a polyhydric alcohol according to the present invention is a two-stage reaction including the aldol condensation reaction and the crossed Cannizzaro reaction in the presence of a base catalyst comprising a carbonate as a principal ingredient, and said reaction is represented by the following reaction formulae including the main reaction and the side reaction.

The following reaction formulae apply to a typical reaction example of the present invention in the case where n-butyhaldehyde (hereinafter referred to as "NBAL") is reacted with trimethylolpropane (hereinafter referred to as "TMP").

(1) Aldol condensation reaction

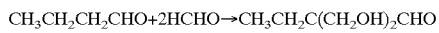

(2) Crossed cannizzaro reaction

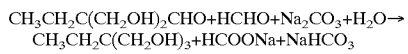

(3) Reaction in which hydrogencarbonate is converted into carbonate

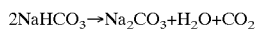

The carbonate, which is a catalyst and a reactional substance in the crossed Cannizzaro reaction, is consumed as a formic acid salt in the reaction system.

The aliphatic aldehyde represented by the general formula (I) according to the present invention is that having at least two hydrogen atoms at the α-position, and is exemplified by propionaldehyde, n-butyhaldehyde, acetaldehyde, pentanal and hexanal, octanal, decanal, dodecanal, icosanal and docosanal. At least two compounds among them may be used in the form of a mixture as starting raw materials.

The formaldehyde to be used in the process according to the present invention may be an aqueous solution of formaldehyde or solid paraformaldehyde, and an appropriate formaldehyde is selected for use according to the objective polyhydric alcohol.

The amount of the formaldehyde to be used in the present process varies depending upon the type of the objective polyhydric alcohol in terms of the theoretical molar amount of formaldehyde. For example, in the case where the objective TMP is produced by the reaction between formaldehyde and NBAL in which R in the general formula (I) is an ethyl group ($CH_3CH_2$) at the theoretical molar ratio of formaldehyde to the NBAL being 3.0, the practical molar ratio thereof is 3 to 6, and preferably 3.05 to 4.0.

Also, in the case where the objective pentaerythritol (hereinafter referred to as "PE") is produced by the reaction between formaldehyde and acetaldehyde (hereinafter referred to as "AAL") in which R in the general formula (I) is hydrogen (H) at the theoretical molar ratio of formaldehyde to the AAL being 4.0, the practical molar ratio thereof is 4.0 to 6.0 and preferably 4.1 to 5.0.

The base catalyst to be used in the aldol condensation reaction and the crossed Cannizzaro reaction according to the present invention, comprises a carbonate as a principal ingredient. As shown by the reaction formula (VI), the compound to be consumed in the course of the crossed Cannizzaro reaction is a carbonate, and a hydrogencarbonate which is formed in the course of the crossed Cannizzaro reaction is converted into the carbonate as shown by the reaction formula (VII).

The aforestated base catalyst may be a carbonate or a mixture of a carbonate and a hydrogencarbonate that are usually available on the market as industrial chemicals. Alternatively the catalyst may be produced starting from the hydrogencarbonate that has been formed by the oxidation or hydrolysis of a formic acid salt. The carbonate may be the salt of any of sodium, potassium, lithium, calcium and ammonium, of which the sodium salt is most general in the case of industrially performing the process of the present invention.

With regard to the amount of the base catalyst to be used in the reaction, the molar ratio of the base expressed in terms of a hydrogencarbonate to an aliphatic aldehyde represented by the general formula (I), is 1 to 2. In order to obtain the objective polyhydric alcohol in high selectivity by suppressing the formation of by-products, the molar ratio needs to be regulated in compliance with the type of the aliphatic aldehyde to be used as a starting raw material. For example, the molar ratio thereof is 1.0 to 1.2 in the case of the aliphatic aldehyde being NBAL, and it is 1.0 to 1.3 in the case of the aliphatic aldehyde being AAL.

The temperature of the reaction between the aliphatic aldehyde and formaldehyde in the process of the present invention is usually 45 to 120° C., preferably 60 to 110° C., and the optimum reaction temperature varies depending upon the type of the aliphatic aldehyde to be used in the reaction.

For example, in the case of producing PE from formaldehyde and AAL, the reaction temperature is 50 to 105° C. In the case of producing TMP from formaldehyde and NBAL, the reaction temperature is 65 to 110° C., and it is preferable to set the aldol condensation reaction temperature on 65 to 110° C., distil away 2-ethylacrylaldehyde (2-ethylacrolein) from the reaction system, and thereafter mature the reactants in the reaction system at 95 to 110° C. for 10 to 30 minutes to complete the crossed Cannizzaro reaction. It is also preferable in this case to pressurize the inside of the reaction system by means of an inert gas such as nitrogen to maintain the reaction temperature at a prescribed level.

The 2-substituted-2-alkenal represented by the general formula (II) is formed by the dehydration reaction of the 2-substituted-2-alkenal-1 in which one mol of formaldehyde is added to an aliphatic aldehyde in the aldol condensation reaction in the reaction formula (V). Accordingly, the 2-substituted-2-alkenal-1 varies depending on the type of the aliphatic aldehyde to be used as a starting material in the reaction, which is exemplified by acrolein, methylacrolein, ethylacrolein, and propylacrolein, etc.

In the process of the present invention, the 2-substituted-2-alkenal may be separated in the purification process of the polyhydric alcohol product, but it is preferable to separate and recover it from the reaction system, simultaneously with the main reaction on the way or separately from the main reaction, and thereafter the crossed Cannizzaro reaction is completed, and it is possible to increase the yield of polyhydric alcohol by circulating to use the recovered 2-substituted-2-alkenal.

That is to say, it is preferable to separate the 2-substituted-2-alkenal while the molar consumption ratio of the base catalyst to the aliphatic aldehyde is in the range of 0.50 to 0.95. The separation and recovery of the 2-substituted-2-alkenal are readily practicable by means of distillation under vacuum, atmospheric, or increased pressure. The loss due to the side reaction of 2-substituted-2-alkenal can be prevented by removing the by-produced 2-substituted-2-alkenal outside the reaction system prior to the completion of the crossed Cannizzaro reaction.

In the process of the present invention, the aldol condensation reaction as the first stage reaction and the crossed Cannizzaro reaction as the second stage reaction may be put into practice under the reaction conditions distinguished from each other, or in the same reactor in a consecutive manner without distinguishing from each other.

In the case of multi-stage continuous reaction system, the 2-substituted-2-alkenal thus recovered can be taken out from a second or third stage reaction kettle and thereafter circulated through a first stage reaction kettle, whereas in the case of batchwise reaction system, the 2-substituted-2-alkenal thus recovered can be circulated to the next reaction system.

The base catalyst comprising a carbonate as a principal ingredient is converted into a formic acid salt in the crossed Cannizzaro reaction, and thus the molar consumption ratio of the base catalyst corresponds to the molar formation ratio of the formic acid salt, by which the separating time of 2-substituted-2-alkenal can be decided.

Since the base catalyst to be used in the process according to the present invention comprises a carbonate as a principal ingredient and further, the reaction in which the hydrogencarbonate is converted to the carbonate as shown by the reaction formula (VII) takes place simultaneously with the crossed Cannizzaro reaction as the second stage reaction, the second stage reaction is accompanied by the generation of gaseous carbon dioxide at the time of reaction. It is, therefore, preferable that the reaction be carried out discontinuously or continuously, while discharging outside the reaction system, low boiling 2-substituted-2-alkenal represented by the general formula (II) as well as the gaseous carbon dioxide.

In the present invention, the 2-substituted-2-alkenal recovered by the method as mentioned above is reacted with water and formaldehyde, and thereafter is circulated to be used. Thus, the 2-substituted-2-alkenal which is inferior in reactivity changes into the 2-substituted-2-alkanal-1 or the 2-substituted-2-alkanal-2 which is superior in reactivity, making it possible to decrease the amount of formaldehyde to be used in the process for producing a polyhydric alcohol and to obtain the objective polyhydric alcohol in a high selectivity.

Further, in the present invention, the 2-substituted-2-alkenal is reacted with water and formaldehyde, and thereafter is circulated into the stage of aldol condensation reaction, thereby making it possible to prevent the loss due to the side reaction of 2-substituted-2-alkenal and to obtain the objective polyhydric alcohol in a high selectivity.

The reaction between the 2-substituted-2-alkenal and water can also be carried out without use of a catalyst. Accordingly, a solution containing the 2-substituted-2-alkanal-1 can be obtained, by such a method as, for example, reacting the mixture itself of 2-substituted-2-alkenal and water, which has been recovered using an azeotropic distillation before the completion of the crossed Cannizzaro reaction, by heating and agitating the mixture at the boiling temperature or lower of the mixture. The solution containing the 2-substituted-2-alkanal-1 is mixed with formaldehyde in the presence of a base catalyst, and thereafter is reacted with an aliphatic aldehyde to be able to produce a polyhydric alcohol.

Also, as a method for the reaction of the 2-substituted-2-alkenal and formaldehyde, in the first place, the 2-substituted-2-alkenal, formaldehyde and a base catalyst solution comprising a carbonate as a principal ingredient are mixed, and then an aliphatic aldehyde is added dropwise at a constant rate into the resultant mixture, or in advance, the 2-substituted-2-alkenal and water are reacted, and then formaldehyde and a base catalyst are added into the 2-substituted-2-alkanal-1 thus obtained and reacted with an aliphatic aldehyde to produce a polyhydric alcohol.

The temperature in the reaction between the 2-substituted-2-alkenal and water or formaldehyde is preferably 45 to 120° C. But it is necessary to set up the temperature at the azeotropic temperature or lower of the 2-substituted-2-alkenal, and for that purpose, it may be possible to pressurize the inside of the reaction system by means of an inert gas such as nitrogen. The reaction time varies with the type of 2-substituted-2-alkenal, but it is usual, for example, to appropriately select the time between 5 to 120 minutes.

In the reaction among the 2-substituted-2-alkenal, water and formaldehyde, an acid such as a formic acid, a sulfuric acid, and a phosphoric acid, or a base catalyst used in the aldol condensation reaction and the crossed Cannizzaro reaction is used as a catalyst. Also, the reaction can be carried out in the absence of a catalyst.

The 2-substituted-2-alkenal has an unsaturated group and is prone to polymerize to form an impurity. However, according to the present invention, the polymerization of 2-substituted-2-alkenal can be prevented and a polyhydric alcohol can be produced in a high selectivity, by previously subjecting the 2-substituted-2-alkenal to the reaction with water and formaldehyde as described above.

In order to promote the selectivity of a polyhydric alcohol, it is preferable to introduce an aliphatic aldehyde into the reaction system of the 2-substituted-2-alkenal, water and formaldehyde, in a situation where the reaction thereof is raised as high as possible. Therefore, it is preferable to set up a molar ratio of the 2-substituted-2-alkenal against the aliphatic aldehyde as a raw material to less than 0.01, preferably to less than 0.001 prior to the introduction of the aliphatic aldehyde.

There are available several methods for isolating the objective polyhydric alcohol from the reaction liquid thus obtained, for example, a method comprising the steps of firstly neutralizing the excess alkali remaining in the resultant reaction liquid by the use of formic acid, subsequently distilling away the residual formaldehyde under a pressure of 0.05 to 0.40 MPa (G), and thereafter usually extracting with a solvent or recrystallizing the objective polyhydric alcohol. However, the aforesaid method varies in its procedures depending upon the physical properties of the objective polyhydric alcohol, especially the difference in solubility in water and the like properties.

In the case of producing TMP, for example, the objective TMP is separated from a formic acid salt by means of solvent extraction. The solvent to be used effectively therein may be the same as a starting raw material, that is, NBAL, or different therefrom including a ketone exemplified by methyl ethyl ketone and methyl isobutyl ketone, an alcohol exemplified by isobutyl alcohol and isopropyl alcohol, an ester exemplified by butyl acetate, and a mixture of at least two of them.

In the case of producing PE from formaldehyde and AAL in which R is hydrogen atom in the general formula (I), the resultant reaction liquid is concentrated, cooled and subjected to crystallization and separation repeatedly to separate PE from the formic acid salt in the aqueous solution by means of solid-liquid separation. The PE thus separated in the form of cake is washed with water and dried into a finished product.

On the other hand, the formic acid salt that has been separated into a water phase is concentrated and recovered as a byproduct by a conventional method, after a treatment with activated carbon as a preliminary treatment for removing organic impurities other than the formic acid salt or without any preliminary treatment. Alternatively, the formic acid salt is converted into a base compound comprising a hydrogencarbonate as a principal ingredient in the presence or absence of oxygen molecules in the presence of a noble metal catalyst or a nickel catalyst. Thus the formic acid is recovered in the form of a base compound.

According to the present invention, in the process for producing a polyhydric alcohol by reacting an aliphatic aldehyde with formaldehyde using a base catalyst comprising a carbonate as a principal ingredient, it is made possible to easily produce the objective polyhydric alcohol in high selectivity and high efficiency by recycling the by-produced 2-substituted-2-alkenal low in an added value, whereby new byproduction of said 2-substituted-2-alkenal is substantially prevented.

Consequently, the process according to the present invention is industrially advantageous to a great extent, since it enables a high-quality polyhydric alcohol to be easily produced in high yield from an aliphatic aldehyde and formaldehyde without discharging outside the reaction system, except for a minimum requirement, the 2-substituted-2-alkenal low in an added value which has heretofore been inevitably by-produced and discharged.

In the following, the present invention will be described in more detail with reference to comparative examples and working examples, which however shall not limit the present invention thereto.

In the following working examples and comparative examples, the selectivity to the objective polyhydric alcohol (on the basis of the consumed aldehyde) is the molar ratio of the production of the objective polyhydric alcohol to the total consumption of an aliphatic aldehyde and 2-substituted-2-alkenal.

EXAMPLE 1

[Preparation of TMP from NBAL and Formaldehyde]

[First stage reaction]

In a 30-liter tank type reactor were placed under mixing, 8200 g (109.2 moles) of aqueous solution of formaldehyde having a concentration of 40% by weight and 9548 g (37.5 moles ) of a basic aqueous solution containing sodium hydrogencarbonate and sodium carbonate in a molar ratio of 2:98 and having a concentration of 33% by weight expressed in terms of sodium hydrogencarbonate. Then, the resultant mixture in the reactor was pressurized up to 0.10 MPa (G) by means of nitrogen gas, and thereafter heated to raise the temperature thereof up to 80° C. under stirring. Then, 2464 g (34.1 moles) of NBAL was added in the mixture at a constant rate over a period of 45 minutes, while the temperature thereof was gradually raised from 80° C. up to a highest controlled temperature of 90° C. Subsequently, the temperature thereof was raised to 98° C. at a constant pressure of 0.10 MPa (G), and the reaction was continued for 15 minutes, while $CO_2$ which was generated during the course of the reaction was discharged outside the reaction system at every necessary time. Thereafter, the temperature and pressure in the reactor were gradually lowered, and the reaction was continued for further 10 minutes, while 2-ethylacrolein (hereinafter referred to as "ECR") as a low boiling distillate and a part of water as an azeotropic component together with the generated $CO_2$ were distilled away from the top portion of the reactor to recover ECR, and the timing for recovery was that the molar consumption ratio of the base catalyst to NBAL was maintained in the range of 0.5 to 0.95. For that timing, the reaction was continued over a period of 10 minutes. The amount of the recovered distillate was 620 g, in which the amount of the ECR was 495.6 g (5.90 moles) including that dissolved in water. After the recovery of the ECR, the reaction was continued at 98 to 100° C. over further 30 minutes. The amount of $CO_2$ that was discharged throughout the reaction was 770 g (17.5 moles). As a result of analysis of 18822 g of the remaining reaction liquid, said liquid contained 17.82% by weight of TMP, and the selectivity to TMP (on the basis of the aldehyde consumed) was 88.8 mol %.

[Second stage reaction] [In the case where ECR and water were reacted in the absence of a catalyst]

620 g (ECR: 5.90 moles) of the total amount of the ECR layer and the water layer recovered in the first stage reaction of Example 1 was mixed with 8000 g of water. Then, the resultant mixture in the reactor was pressurized up to 0.10 MPa (G) by means of nitrogen gas, and thereafter heated to raise the temperature thereof up to 80° C. under stirring, and the reaction was continued at this temperature over a period of 10 minutes. The remaining amount of ECR in the reaction liquid was 2 g (a molar ratio/NBAL raw material=0.0007), into which 8200 g (109.2 moles) of aqueous solution of formaldehyde having a concentration of 40% by weight and 9548 g (37.5 moles) of a basic aqueous solution containing sodium hydrogencarbonate and sodium carbonate in a molar ratio of 2:98 and having a concentration of 33% by weight expressed in terms of sodium hydrogencarbonate were added. Then, 2464 g (34.1 moles) of NBAL was added in the mixture at a constant rate over a period of 45 minutes, while the temperature thereof was gradually raised from 80° C. up to a highest controlled temperature of 98° C. Subsequently, the temperature thereof was raised to 98° C. at a constant pressure of 0.10 MPa (G), and the reaction was continued for 10 minutes, while $CO_2$ which was generated during the course of the reaction was discharged outside the reaction system at every necessary time. Thereafter, the pressure in the reactor was gradually lowered, while ECR as a low boiling distillate and a part of water as an azeotropic component together with the generated $CO_2$ were distilled away from the top portion of the reactor to recover ECR, and the timing for recovery was conducted in the same way as the first reaction stage and the reaction was continued for 10 minutes. The amount of the recovered distillate was 650 g, in which the amount of the ECR was 499 g (5.95 moles) including that dissolved in water. After the recovery of the ECR, the reaction was continued at 98 to 100° C. over further 30 minutes. As a result of analysis of 27421 g of the remaining reaction liquid, said liquid contained 15.18% by weight of TMP, and the selectivity to TMP (on the basis of the aldehyde consumed) was 91.1 mol %.

COMPARATIVE EXAMPLE 1

[In the case where ECR was not recovered]

In the same manner as in the first stage reaction of Example 1, in a 30L tank type reactor were placed under mixing, 8200 g (109.2 moles) of aqueous solution of formaldehyde having a concentration of 40% by weight and 9548 g (37.5 moles) of a basic aqueous solution containing sodium hydrogencarbonate and sodium carbonate in a molar ratio of 2:98 and having a concentration of 33% by weight expressed in terms of sodium hydrogencarbonate. Then, the resultant mixture in the reactor was pressurized up to 0.10 MPa (G) by means of nitrogen gas, and thereafter heated to raise the temperature thereof up to 80° C. under stirring. Then, 2464 g (34.1 moles) of NBAL was added in the mixture at a constant rate over a period of 45 minutes, while the temperature thereof was gradually raised from 80° C. up to a highest controlled temperature of 98° C. After the addition of the NBAL, the reaction was continued for 10 minutes, while the pressure and the temperature in the reaction system were maintained at 0.10 MPa (G) and 98° C., respectively. Thereafter, the pressure in the reactor was gradually lowered, and the reaction was continued for further 30 minutes, while the by-produced ECR was not recovered, and $CO_2$ which was generated during the course of the reaction was discharged outside the reaction system at every necessary time. The amount of $CO_2$ gas discharged through the reaction was 775 g. As a result of analysis of 19437 g of the remaining reaction liquid, said liquid contained 17.7% by weight of TMP, and the selectivity to TMP (on the basis of the aldehyde consumed) was 76.5 mol %.

EXAMPLE 2

[In the case where ECR was reacted with an aqueous solution of formaldehyde in the presence of a catalyst]

6775 g (90.24 moles) of aqueous solution of formaldehyde having a concentration of 40% by weight and 7896 g (31.02 moles) of a basic aqueous solution having a concentration of 33% by weight expressed in terms of sodium hydrogencarbonate were mixed. Then, the resultant mixture in the reactor was pressurized up to 0.10 MPa (G) by means of nitrogen gas, and thereafter heated to raise the temperature thereof up to 80° C. under stirring, to which 650 g of the total amount of the ECR layer and water layer recovered from the second step reaction of Example 1 was added, and the reaction was continued for a period of 10 minutes. The remaining amount of ECR in the reaction liquid was 2 g (a molar ratio/NBAL raw material=0.0008), to which 2035 g (28.2 moles) of NBAL was added at a constant rate over a period of 45 minutes, while the temperature thereof was gradually raised from 80° C. up to a highest controlled temperature of 98° C. After the addition of NBAL, the reaction was continued for further 10 minutes, maintaining the pressure and the temperature at 0.10 MPa (G) and 98° C., respectively, while $CO_2$ which was generated during the course of the reaction was discharged outside the reaction system at every necessary time. Thereafter, the pressure in the reactor were gradually lowered, while ECR as a low boiling distillate and a part of water as an azeotropic component together with the generated $CO_2$ were distilled away from the top portion of the reactor to recover ECR, and the timing for recovery was conducted in the same way as the first reaction stage of Example 1. The amount of the recovered distillate was 654 g, in which the amount of the ECR was 498.8 g (5.94 moles) including that dissolved in water. After the recovery of the ECR, the reaction was continued at 98 to 100° C. over further 30 minutes. As a result of analysis of 16052 g of the remaining reaction liquid, said liquid contained 21.18% by weight of TMP, and the selectivity to TMP (on the basis of the aldehyde consumed) was 90.0 mol %.

COMPARATIVE EXAMPLE 2

[In the case where ECR was added together with NBAL]

In the same manner as in the first stage reaction of Example 1, 6775 g (90.24 moles) of aqueous solution of formaldehyde having a concentration of 40% by weight and 7896 g (31.02 moles) of a basic aqueous solution containing sodium hydrogencarbonate and sodium carbonate in a molar ratio of 2:98 and having a concentration of 33% by weight expressed in terms of sodium hydrogencarbonate. Then, the resultant mixture in the reactor was pressurized up to 0.10 MPa (G) by means of nitrogen gas, and thereafter heated to raise the temperature thereof up to 80° C. under stirring, to which total amount of the water layer recovered in the first stage reaction of Example 1 was added, and then the homogeneous mixture of all the ECR layer (ECR 5.94 moles) and 2023 g (28.2 moles) of NBAL was added at a constant rate over a period of 45 minutes, while the temperature thereof was gradually raised from 80° C. up to a highest controlled temperature of 98° C. After that, the reaction was continued for 10 minutes, maintaining the temperature at 98° C. $CO_2$ gas which was generated during the course of the reaction was discharged outside the reaction system at every necessary time. Thereafter, the pressure in the reactor were gradually lowered, while ECR as a low boiling distillate and a part of water as an azeotropic component together with the generated $CO_2$ were distilled away from the top portion of the reactor to recover ECR. The timing for recovery was conducted in the same way as the first reaction stage of Example 1, and the reaction was continued for further 10 minutes. The amount of the recovered distillate was 654 g, in which the amount of the ECR was 500.6 g (5.96 moles) including that dissolved in water. After the recovery of ECR, the reaction was continued for still more 30 minutes at 90 to 100° C. As a result of analysis of 116030 of the remaining reaction liquid, said liquid contained 19.33% by weight of TMP, and the selectivity to TMP (on the basis of the aldehyde consumed) was 82.0 mol %.

EXAMPLE 3

[Preparation of PE from AAL and formaldehyde]

[First stage reaction]

6870 g (91.5 moles) of aqueous solution of formaldehyde having a concentration of 40% by weight, 1314 g (12.4 moles) of a sodium carbonate, and 3066 g of water were mixed. The resultant mixture in the reactor was pressurized up to 0.10 MPa (G) by means of nitrogen gas, and thereafter heated to raise the temperature thereof up to 60° C. under stirring, to which 893.2 g (20.3 moles) of AAL was added dropwise at a constant rate over a period of 30 minutes, while the temperature thereof was gradually raised from 60° C. up to a highest controlled temperature of 75° C. After that, the reaction was continued for 15 minutes, maintaining the pressure and the temperature at 0.10 MPa (G) and 80° C., respectively, while $CO_2$ which was generated during the course of the reaction was discharged outside the reaction system at every necessary time. Thereafter, the temperature and the pressure in the reactor were gradually lowered, while acrolein (hereinafter referred to as "ACR") as a low boiling distillate and a part of water as an azeotropic component together with the generated $CO_2$ were distilled away from the top portion of the reactor to recover ACR, and the timing for recovery was between 0.5 to 0.95 molar ratio on the basis of the base catalyst consumed per NBAL, while the reaction was continued for 10 minutes. The amount of the recovered distillate was 320 g, in which the amount of the ACR was 147.8 g (2.64 moles) including that dissolved in water. After the recovery of the ACR. The reaction was continued at 98 to 100° C. for further 30 minutes, and the amount of $CO_2$ gas discharged through the reaction was 536.8 g (12.2 moles). As a result of analysis of 11286 g of the remaining reaction liquid, said liquid contained 16.94% by weight of PE, and the selectivity to PE (on the basis of the aldehyde consumed) was 90.2 mol %.

[Second stage reaction] [In the case where ACR and an aqueous solution of formaldehyde were reacted in the presence of a catalyst]

6870 g (91.5 moles) of aqueous solution of formaldehyde having a concentration of 40% by weight, 1183 g (11.2 moles) of a sodium carbonate, and 3197 g of water were mixed. The resultant mixture in the reactor was pressurized up to 0.10 MPa (G) by means of nitrogen gas, and then the temperature thereof was raised up to 60° C. under stirring, into which 320 g of total amount of the ACR layer and the water layer recovered in the first stage reaction of Example 3 was added, and the reaction was continued for 10 minutes. The remaining amount of ACR in the reaction liquid was 0.8 g (a molar ratio per AAL=0.0009). 893.2 g (20.3 moles) of aqueous solution of AAL was added to the reaction liquid at a constant rate over a period of 30 minutes, while the temperature thereof was gradually raised from 60° C. up to a highest controlled temperature of 75° C. Subsequently, the temperature and the pressure thereof were raised to 98° C. and 0.10 MPa (G), respectively, and the reaction was continued for 15 minutes, while $CO_2$ which was generated during the course of the reaction was discharged outside the reaction system at every necessary time. Thereafter, the temperature and the pressure in the reactor were gradually lowered, while ACR as a low boiling distillate and a part of water as an azeotropic component together with the generated $CO_2$ were distilled away from the top portion of the reactor to recover ECR. The timing for recovery was conducted in the same way as the first reaction stage and the reaction was continued for 10 minutes. The amount of the recovered distillate was 322 g, in which the amount of the ACR was 148.2 g (2.65 moles) including that dissolved in water. After the recovery of the ACR, the reaction was continued at 98 to 100° C. over further 30 minutes. The amount of $CO_2$ gas discharged through the reaction was 540 g (12.3 moles). As a result of analysis of 11436 g of the remaining reaction liquid, said liquid contained 19.49% by weight of PE, and the selectivity to PE (on the basis of the aldehyde consumed) was 91.5 mol %.

What is claimed is:

1. A process for producing a polyhydric alcohol which comprises subjecting formaldehyde and at least one aliphatic aldehyde to an aldol condensation reaction in the presence of a base catalyst comprising a carbonate as a principal component, said aliphatic aldehyde being represented by the formula (I):

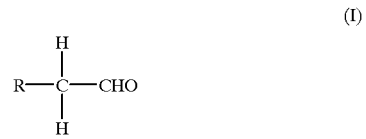

and subsequently subjecting the resultant reaction product to a crossed Cannizzaro reaction, while mixing a solution containing a 2-substituted-2-alkanal-1 with formaldehyde in the presence of said base catalyst, and thereafter reacting the resultant mixture with said aliphatic aldehyde represented by the formula (I), wherein said 2-substituted-2-alkanal-1 being represented by the formula (III):

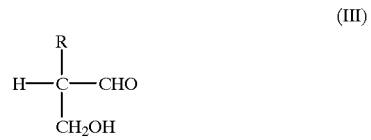

and being obtained by reacting a 2-substituted-2-alkenal which is formed as a byproduct during said aldol condensation reaction with water in the presence or the absence of a catalyst, said 2-substituted-2-alkenal being represented by the formula (II):

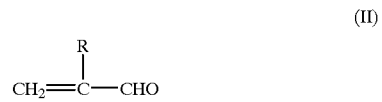

wherein R is a hydrogen atom or a straight-chain or branched aliphatic hydrocarbon group having 1 to 22 carbon atoms.

2. A process for producing a polyhydric alcohol which comprises subjecting formaldehyde and at least one aliphatic aldehyde to an aldol condensation reaction in the presence of a base catalyst comprising a carbonate as a principal component, said aliphatic aldehyde being represented by the formula (I):

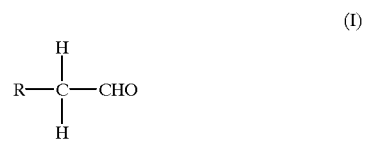

and subsequently subjecting the resultant reaction product to a crossed Cannizzaro reaction, while mixing a solution containing a 2-substituted-2-alkanal-1 represented by the formula (III):

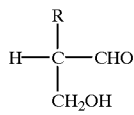

(III)

and a 2-substituted-2-alkanal-2 represented by the formula (IV):

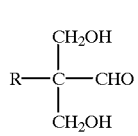

(IV)

with formaldehyde in the presence of said base catalyst, and thereafter reacting the resultant mixture with said aliphatic aldehyde represented by the formula (I), wherein both of said 2-substituted-2-alkanal-1 and said 2-substituted-2-alkanal-2 being obtained by reacting a 2-substituted-2-alkenal which is formed as a byproduct during said aldol condensation reaction with formaldehyde and water in the presence or absence of a catalyst, said 2-substituted-2-alkenal being represented by the formula (II):

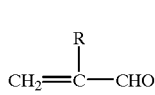

(II)

wherein R is a hydrogen atom or a straight-chain or branched aliphatic hydrocarbon group having 1 to 22 carbon atoms.

3. The process for producing a polyhydric alcohol according to claims 1 or 2, wherein said 2-substituted-2-alkenal formed during the aldol condensation reaction as a byproduct and represented by the formula (II), is separated while the molar consumption ratio of the base catalyst to the aliphatic aldehyde is 0.50 to 0.95.

4. The process for producing a polyhydric alcohol according to claims 1 or 2, wherein said base catalyst is a carbonate or a mixture of a carbonate and a hydrogen carbonate.

5. The process for producing a polyhydric alcohol according to claim 4, wherein said base catalyst contains a hydrogen carbonate which is formed by the oxidation or hydrolysis of a formic acid salt.

6. The process for producing a polyhydric alcohol according to claim 4, wherein said base catalyst is selected from the group consisting of sodium carbonate, potassium carbonate, lithium carbonate, calcium carbonate and ammonium carbonate.

7. The process for producing a polyhydric alcohol according to claims 1 or 2, wherein a molar ratio of said 2-substituted-2-alkenal is less than 0.01 per said aliphatic aldehyde introduced into the aldol condensation reaction prior to the introduction of said aliphatic aldehyde.

8. The process for producing a polyhydric alcohol according to claims 1 or 2, wherein said 2-substituted-2-alkenal formed as a byproduct during the aldol condensation reaction is separated prior to the completion of the crossed Cannizzaro reaction.

9. The process for producing a polyhydric alcohol according to claims 1 or 2, wherein said catalyst used in the reaction of the 2-substituted-2-alkenal with water or formaldehyde is said base catalyst or an acid catalyst.

10. The process for producing a polyhydric alcohol according to claims 1 or 2, wherein trimethylolpropane is produced from formaldehyde and n-butyhaldehyde.

11. The process for producing a polyhydric alcohol according to claims 1 or 2, wherein said base catalyst is used in an amount of 1 to 2 molar ratio expressed in terms of hydrogencarbonate to an aliphatic aldehyde.

12. The process for producing a polyhydric alcohol according to claim 1, wherein the aliphatic aldehyde is n-butyraldehyde; the molar ratio of the formaldehyde to the n-butyraldehyde is 3.05 to 4; the base catalyst is hydrogen carbonate; the molar ratio of the hydrogen carbonate to the aliphatic aldehyde is 1.0 to 1.2; and the aldol condensation is carried out at a temperature of 65 to 110° C.

13. The process for producing a polyhydric alcohol according to claim 1, wherein the aliphatic aldehyde is acetaldehyde; the molar ratio of the formaldehyde to the acetaldehyde is 4.1 to 5.0; the base catalyst is hydrogen carbonate; the molar ratio of the hydrogen carbonate to the aliphatic aldehyde is 1.0 to 1.3; and the aldol condensation is carried out at a temperature of 50 to 105° C.

* * * * *